US008607647B1

(12) United States Patent
Wilson et al.

(10) Patent No.: US 8,607,647 B1
(45) Date of Patent: Dec. 17, 2013

(54) BICYCLE POWER SENSING SYSTEM

(75) Inventors: Matthew R. Wilson, Madison, WI (US); Joshua G. Lohr, Madison, WI (US); Jeffery T. Iverson, Madison, WI (US)

(73) Assignee: Saris Cycling Group, Inc., Madison, WI (US)

( * ) Notice: Subject to any disclaimer, the term of this patent is extended or adjusted under 35 U.S.C. 154(b) by 274 days.

(21) Appl. No.: 13/149,026

(22) Filed: May 31, 2011

(51) Int. Cl.
*G01L 3/02* (2006.01)

(52) U.S. Cl.
USPC ................................ 73/862.31; 73/862.08

(58) Field of Classification Search
USPC .............................. 73/862.08, 862.29, 862.31
See application file for complete search history.

(56) References Cited

U.S. PATENT DOCUMENTS

| | | |
|---|---|---|
| 3,599,482 A | 8/1971 | Rundell |
| 3,695,729 A | 10/1972 | Schwerdhofer |
| 3,927,559 A | 12/1975 | Da Costa et al. |
| 4,020,918 A | 5/1977 | Houskamp et al. |
| 4,062,421 A | 12/1977 | Weber |
| 4,141,248 A | 2/1979 | Bargenda |
| 4,297,877 A | 11/1981 | Stahl |
| 4,423,630 A | 1/1984 | Morrison |
| 4,436,433 A | 3/1984 | Barnes |
| 4,625,551 A | 12/1986 | Carnielli |
| 4,811,612 A | 3/1989 | Mercat |
| 4,875,379 A | 10/1989 | Rohs et al. |
| 4,966,380 A | 10/1990 | Mercat |
| 5,016,478 A | 5/1991 | Mercat |
| 5,018,392 A | 5/1991 | Mercat |
| 5,027,303 A | 6/1991 | Witte |
| 5,031,455 A | 7/1991 | Cline |
| 5,065,633 A | 11/1991 | Mercat |
| 5,167,159 A | 12/1992 | Lucking |
| 5,202,627 A | 4/1993 | Sale |
| 5,256,115 A | 10/1993 | Scholder et al. |
| 5,257,540 A | 11/1993 | Bower et al. |
| 5,591,908 A | 1/1997 | Reid |
| 6,152,250 A | 11/2000 | Shu-Hsien |
| 6,418,797 B1 * | 7/2002 | Ambrosina et al. ....... 73/862.29 |
| 6,688,704 B2 | 2/2004 | Meggiolan |
| 6,886,416 B2 | 5/2005 | Tsay et al. |
| 7,004,862 B2 | 2/2006 | Fukuda |

(Continued)

FOREIGN PATENT DOCUMENTS

| | | |
|---|---|---|
| DE | 3150149 | 6/1983 |
| GB | 2109568 | 6/1983 |
| GB | 2286055 | 8/1995 |

OTHER PUBLICATIONS

"Formula, The Essence of Motion", Formula Engineering, Inc. 13, Lane 227, Shen-Chou Road, Shen-Kang Hsiang, Taichung Hsien, Taiwan, 5 pages, undated.

(Continued)

*Primary Examiner* — Max Noori
(74) *Attorney, Agent, or Firm* — Boyle Fredrickson, S.C.

(57) ABSTRACT

A bicycle power sensing system includes an electronics module that can be separated from a power-measuring hub assembly. The power-measuring hub assembly includes onboard electronics that cooperates with the electronics module when the electronics module is attached to the power-measuring hub assembly. The onboard electronics includes a memory module that stores a calibration value for a torque tube of the power-measuring hub assembly so that the torque tube does not have to be recalibrated after the electronics module is removed from the power-measuring hub assembly.

20 Claims, 6 Drawing Sheets

(56) References Cited

U.S. PATENT DOCUMENTS

| | | |
|---|---|---|
| 7,047,817 B2 | 5/2006 | Lanham |
| 7,062,980 B2 * | 6/2006 | Takamoto et al. ......... 73/862.31 |
| 7,066,558 B2 | 6/2006 | Meggiolan |
| 7,775,128 B2 * | 8/2010 | Roessingh et al. ....... 73/862.191 |
| 7,861,599 B2 * | 1/2011 | Meggiolan ...................... 73/794 |
| 7,975,561 B1 * | 7/2011 | Ambrosina et al. ..... 73/862.338 |
| 8,336,400 B2 * | 12/2012 | Lassanske .................. 73/862.29 |
| 2005/0275561 A1 * | 12/2005 | Kolda et al. .............. 340/870.07 |
| 2006/0158868 A1 | 7/2006 | Palmer et al. |

OTHER PUBLICATIONS

"Ultra Light Weight Fiber for Road Racing", 2004 Novatec, 1 page.

* cited by examiner

BICYCLE POWER SENSING SYSTEM

BACKGROUND OF THE INVENTION

1. Field of the Invention

The invention relates to bicycle power sensing systems and, more particularly, to a bicycle power sensing system having a power-measuring hub assembly that includes a torque tube.

2. Discussion of the Related Art

Bicycle power sensing systems or power meters are known. A known system incorporates a power-measuring hub assembly that can measure torque values at a torque tube which couples a driven sprocket to the hub of a driven wheel.

Bicyclists using a power sensing system of this type deliver power through the pedals, crank arms, and crank sprockets to the driven sprockets. In this way, the torque values measured by the power-measuring hub assemblies at the toque tube are indicative of the power levels outputted by the bicyclists.

SUMMARY OF THE INVENTION

The inventors have recognized that prior art power-measuring hub assemblies that use torque tubes require specific calibration values for each hub. The inventors have further recognized that, when disassembled and reassembled, these prior art power-measuring hub assemblies must be recalibrated during reassembly. The inventors have further recognized that end users are typically unable to recalibrate torque tubes, whereby the end users of such prior art power-measuring hub assemblies are typically unable to service, repair, or even trouble-shoot such prior art power-measuring hub assemblies, themselves. The inventors have recognized that instead of users of such prior art power-measuring hub assemblies disassembling the power-measuring hub assemblies, and sending certain components to a service center for diagnostic testing, since recalibrations of the toque tubes are required, such users must send the entire power-measuring hub assemblies or the wheels in which the power-measuring hub assemblies are mounted to a service center for service, repair, or trouble-shooting. The inventors have also recognized that when such prior art power-measuring hub assemblies fail, the failures typically occur in fewer than all of the electronic components within the power-measuring hub assemblies, yet repairs of such prior art power-measuring hub assemblies typically require either recalibrations or replacements of the torque tubes. The present invention contemplates a bicycle power sensing system that addresses these and other inventor-identified problems and drawbacks of the prior art.

In accordance with an aspect of the present invention, a bicycle power sensing system is provided that allows some electronic components to be removed, serviced, and/or replaced, without removing, servicing, and/or replacing a memory module that stores a calibration value. The bicycle power sensing system includes a power-measuring hub assembly that may include a hub for supporting a driven wheel of a bicycle from an axle, and a torque tube that can accept a driving torque and is connected to the hub. The torque tube transmits the driving torque for rotating the driven wheel so that the torque value can be determined. The torque tube may include a sensor that detects the driving torque and a memory module that operably communicates with the sensor and stores a calibration value for the torque tube. The sensor may be in the form of one or more strain gauges on the torque tube, and the calibration value for the torque tube may correspond to a calibration value of a strain gauge amplifier. An electronics module may be removably connected to at least one of the sensor and the memory module so that the electronics module can determine the driving torque experienced by the torque tube. This may allow the electronics module to be removed from the power-measuring hub assembly without disrupting the memory module upon which the calibration value is stored. Doing so may allow for inspection, servicing, and/or repair of various parts of the power-measuring hub assembly without requiring a user to send the entire power-measuring hub assembly or a wheel in which the power-measuring hub assembly is mounted to a service center for recalibration.

In accordance with another aspect of the present invention, the memory module may be connected to at least one of the hub and torque tube through a first connection interface. The electronics module may communicate with at least one of the sensor and memory module, and may be connected to at least one of the hub and torque tube through a second connection interface. The second connection interface may differ from the first connection interface so that the electronics module can be removed from the hub and/or torque tube while the memory module remains connected to the hub and/or torque tube. This may allow for inspection, servicing, and/or repair of various parts of the power-measuring hub assembly without requiring a user to send the entire power-measuring hub assembly or a wheel in which the power-measuring hub assembly is mounted to a service center for recalibration.

In accordance with another aspect of the present invention, the electronics module may define (i) a connected position in which the electronics module is connected to the torque tube so that the sensor and memory module of the torque tube communicate with the electronics module to determine the driving torque, and (ii) a disconnected position in which the electronics module is separated from the torque tube so that the sensor and memory module do not communicate with the electronics module. This may be achieved with a connector assembly having (i) a first connector that is provided on the torque tube and is in communication with at least one of the sensor and the memory module, and (ii) a second connector that is provided on and is in communication with the electronics module. The first and second connectors engage and disengage each other when the electronics module is in the connected and disconnected positions, respectively. The first and second connectors may include a receptacle having a flexible conductor tab that can be received in the receptacle. This may allow the electronics module to release from the remainder of the power-measuring hub assembly which may allow for inspection, servicing, and/or repair of various parts of the power-measuring hub assembly without requiring a user to send the power-measuring hub assembly or a wheel in which the power-measuring hub assembly is mounted to a service center for recalibration.

In accordance with yet another aspect of the present invention, the memory module is fixedly connected to the at least one of the hub and torque tube. This may integrate the memory module into the hub and/or torque tube so that the memory module is substantially inseparable from the hub and/or torque tube. The torque tube further may include a flange, to which the memory module may be connected. The memory module may be connected to the torque tube flange by at least one of an adhesive material and a potting material. This may fix the memory module to the torque tube so that the specific calibration value(s) of that particular torque tube remain undisturbed and the memory module physically connected to the torque tube, which may allow other portions of the power-measuring hub assembly to be removed from the torque tube and allow for inspection, servicing, and/or repair of various parts of the power-measuring hub assembly without requiring a recalibration of the torque tube.

In accordance with yet another aspect of the present invention, the electronics module may include an enclosure that may engage at least one of the hub and the torque tube in a manner that selectively connects the electronics module to at least one of the sensor and memory module. The enclosure may include an opening that is aligned with a battery holder of the electronics module, allowing the battery to be inserted into and removed from the battery holder. The enclosure may allow access to a data port of the electronics module for transferring data between the electronics module and a computer. This may allow for battery changing, firmware upgrading, failure diagnosis, and performance data logging of the power-measuring hub assembly by way of the electronics module, without requiring a recalibration of the torque tube.

In accordance with yet another aspect of the present invention, the enclosure includes a tapering wall that engages the hub. The enclosure and hub may engage each other at an abutment between the tapering wall and an inner circumferential surface of the hub. The enclosure may include an end wall that engages or faces the torque tube. The enclosure end wall and torque tube may engage each other at a location that is concentrically inside of the hub, such that the enclosure is at least partially longitudinally nested within the hub. A seal may be provided between the enclosure and hub and/or torque tube and the enclosure may be longitudinally held in place with a cap so that the enclosure compresses the seal between it and the hub and/or torque tube to resist water penetration into the torque tube. This may provide water resistance to the power-measuring hub assembly despite removal and reconnecting of the enclosure with respect to the remainder of the power-measuring hub assembly.

Various other features, objects, and advantages of the invention will be made apparent from the following description taken together with the drawings.

BRIEF DESCRIPTION OF THE DRAWINGS

The drawings illustrate the best mode presently contemplated of carrying out the invention.

In the Drawings.

DETAILED DESCRIPTION OF THE INVENTION

Figure 1:
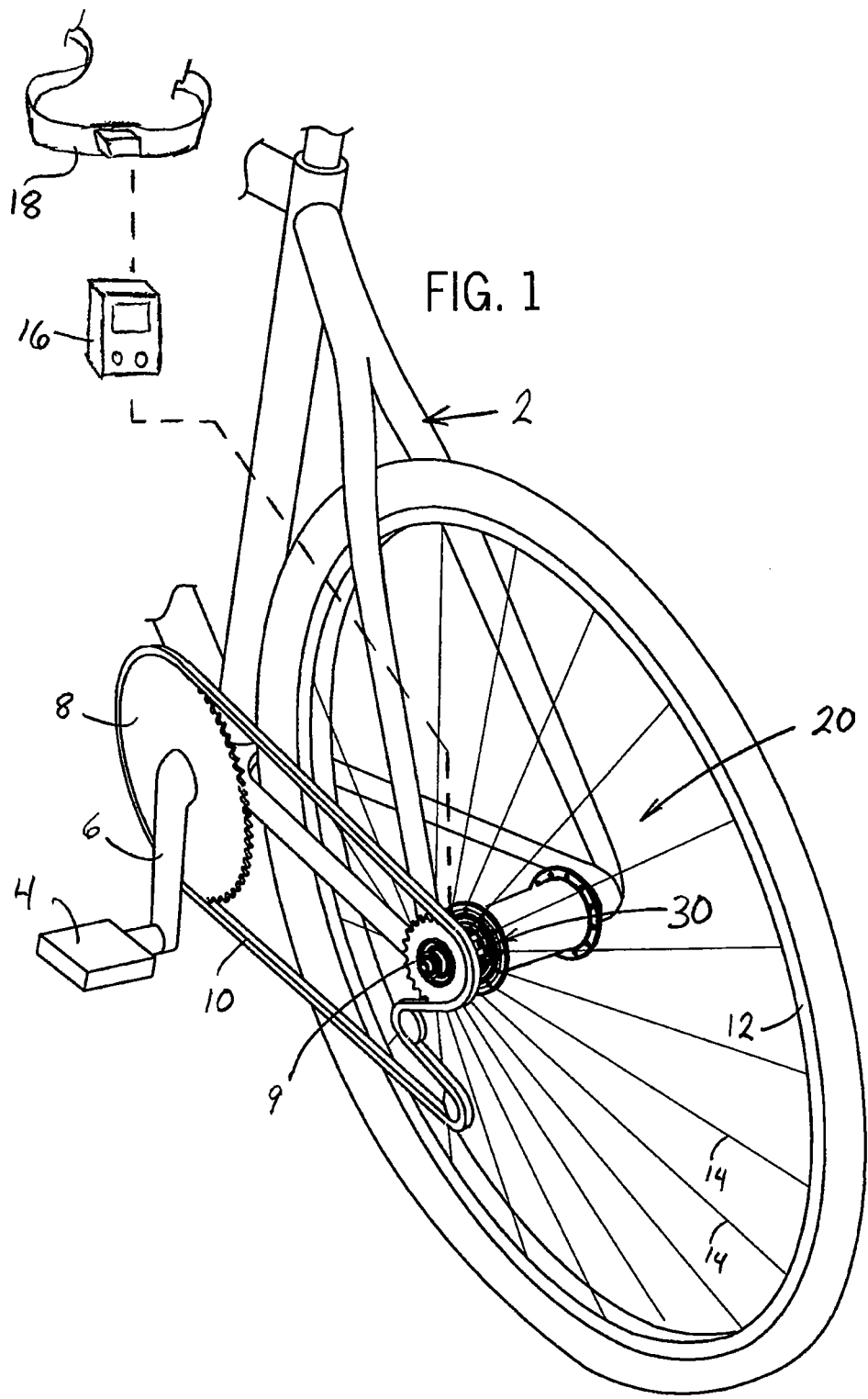
FIG. 1 is an isometric view of a schematic representation of a bicycle power sensing system in accordance with the present invention, in the form of a power-measuring hub assembly.

FIG. 1 shows a schematic isometric view of a portion of a bicycle 2 that incorporates a bicycle power sensing system 20 in accordance with the present invention. The bicycle 2 includes a pair of pedals 4 (only one shown) connected by crank arms 6 (only one shown) to a crank sprocket or front chain ring 8. The crank chain ring 8 is coupled to a driven sprocket 9, which is typically one of several sprockets in a stack or cone of differently sized sprockets, by a chain 10. The driven sprocket 9 is operably coupled to the power-measuring hub assembly 30 of the power sensing system 20, explained in greater detail elsewhere herein. The bicycle 2 is powered by a cyclist providing rotational forces to the crank chain ring 8 via the pedals 4 and crank arms 6. The rotation of the crank chain ring 8 is transferred by the chain 10 to the driven sprocket 9 and thus to the power-measuring hub assembly 30 which carries and rotates a driven rear wheel 12 into rotation via spokes 14 to drive the bicycle 2 into motion.

Still referring to FIG. 1, the bicycle power sensing system 20 includes the power-measuring hub assembly 30 that can measure torque and wheel speed of the driven rear wheel 12. The bicycle power sensing system 20 also includes a computer 16 that can be mounted to the bicycle 2, which may also receive signals from a chest strap monitor 18 that is worn by the cyclist. The chest strap monitor 18 detects heart rate of the cyclist and transmits corresponding heart rate data to computer 16. The power-measuring hub assembly 30 transmits data corresponding to a measured torque and wheel speed of the driven wheel 12 to the computer 16. The chest strap monitor 18 and power-measuring hub assembly 30 may wirelessly transmit data to the computer 16, for example at a signal transmission rate of 2.4 GHz or other suitable rate. Such data can then be integrated or otherwise processed by the computer 16 to display, for example, instantaneous, current, average, and/or maximum biometric information. It is understood that the computer 16 may be programmed to determine, store, and/or display any of a variety of information that is based on the data from the chest strap monitor 18 and/or power-measuring hub assembly 30 acquired during an exercise session, such as instantaneous power, average power and maximum power; instantaneous cadence, average cadence and maximum cadence; instantaneous heart rate, average heart rate and maximum heart rate; as well as typical cycle computer functions such as clock, time, distance and speed information.

Figure 2:
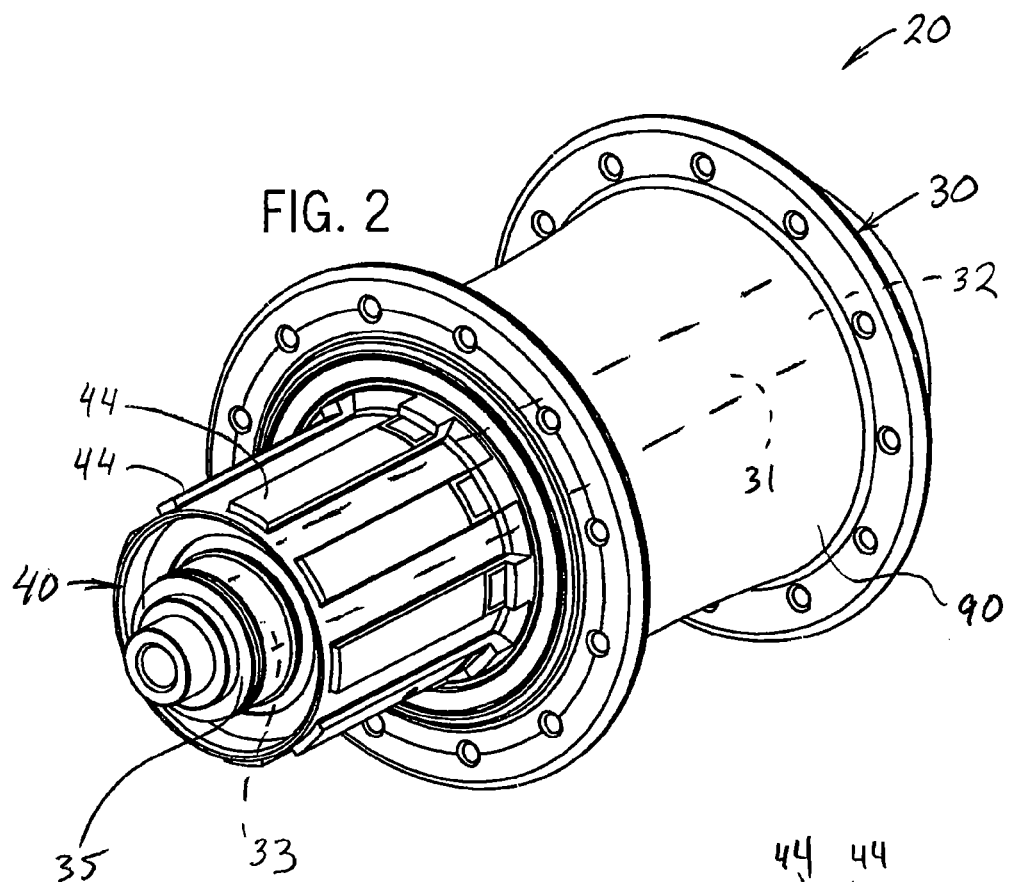
FIG. 2 is an isometric view of the power-measuring hub assembly of the bicycle power sensing system of FIG. 1.
Figure 3:
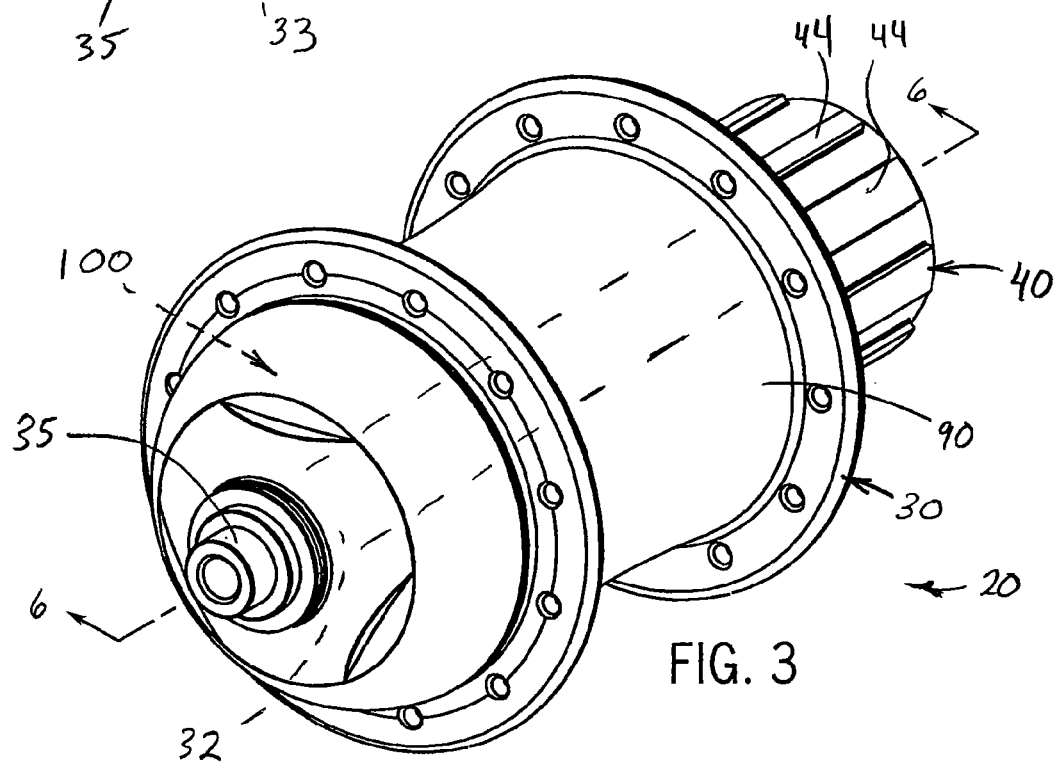
FIG. 3 is another isometric view of the power-measuring hub assembly of the bicycle power sensing system of FIG. 1.
Figure 4:
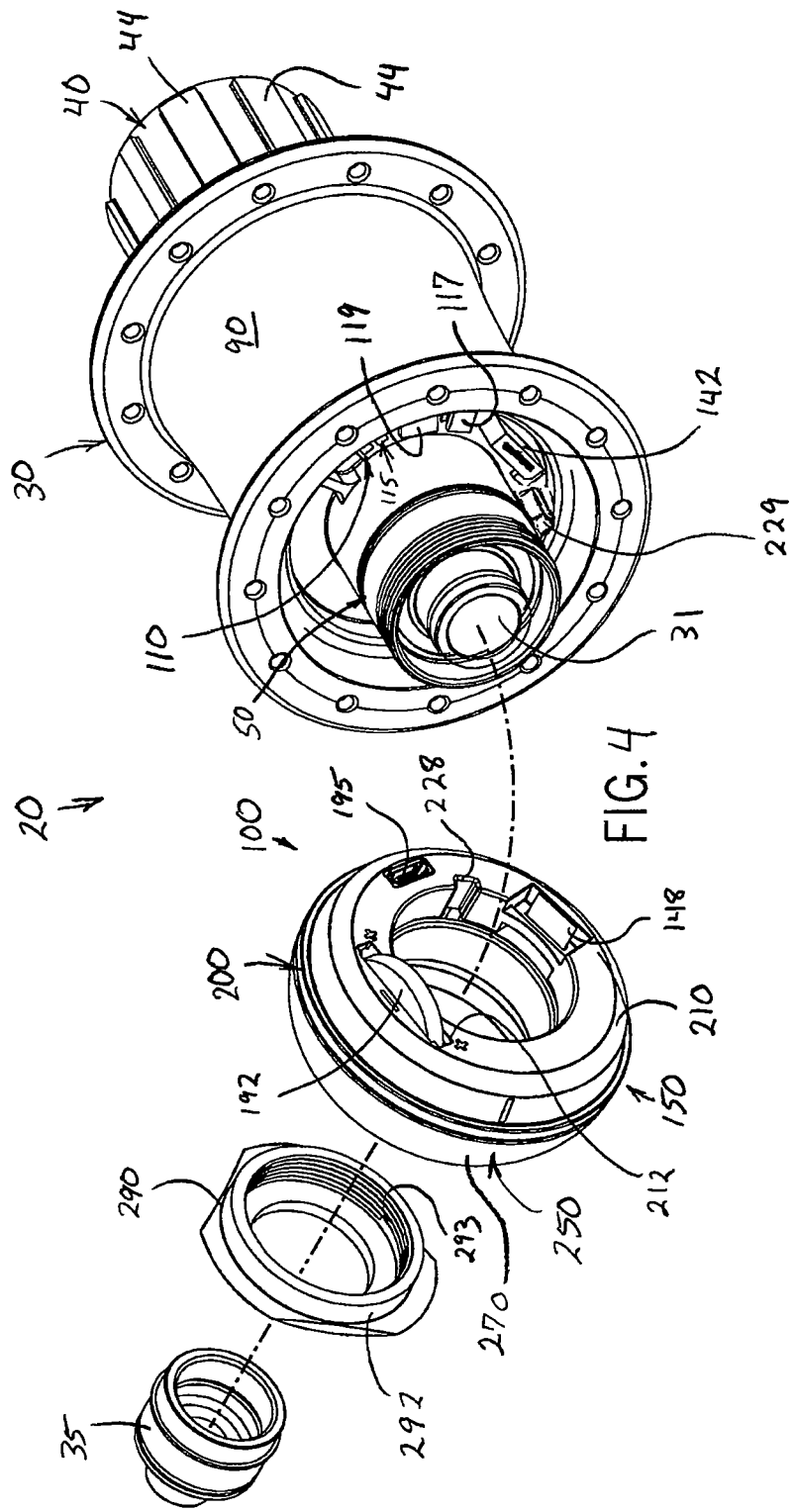
FIG. 4 is a partially exploded isometric view of the power-measuring hub assembly of FIG. 3.

Referring now to FIGS. 2-4, power-measuring hub assembly 30 includes an axle 31 that extends longitudinally through and supports the rest of the power-measuring hub assembly 30. In a manner as is known, axle 31 is configured for engagement with the fork ends or dropouts of bicycle 2. A quick-release skewer extends through axle 31, and engages the fork ends or dropouts of bicycle 2 (FIG. 1) for mounting the power-measuring hub assembly 30 to the bicycle 2. Between the end caps 35 and concentrically outside of the axle 31, the power-measuring hub assembly 30 includes a free hub 40, a torque tube 50 (FIG. 4), a hub shell 90, and an electronics system 100 which is explained in greater detail elsewhere herein.

Figure 5:
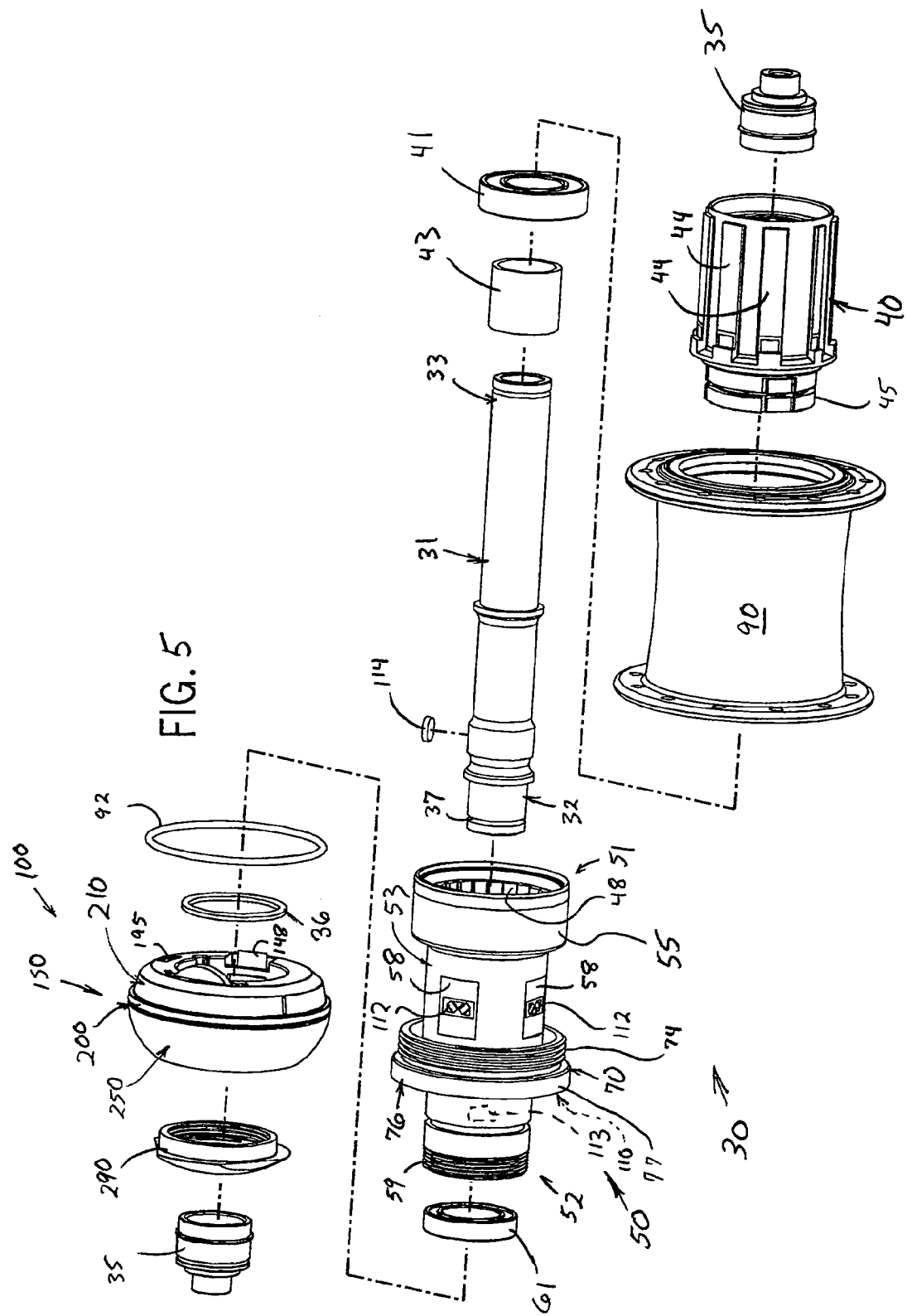
FIG. 5 is an exploded isometric view of the power-measuring hub assembly of FIG. 3.
Figure 6:
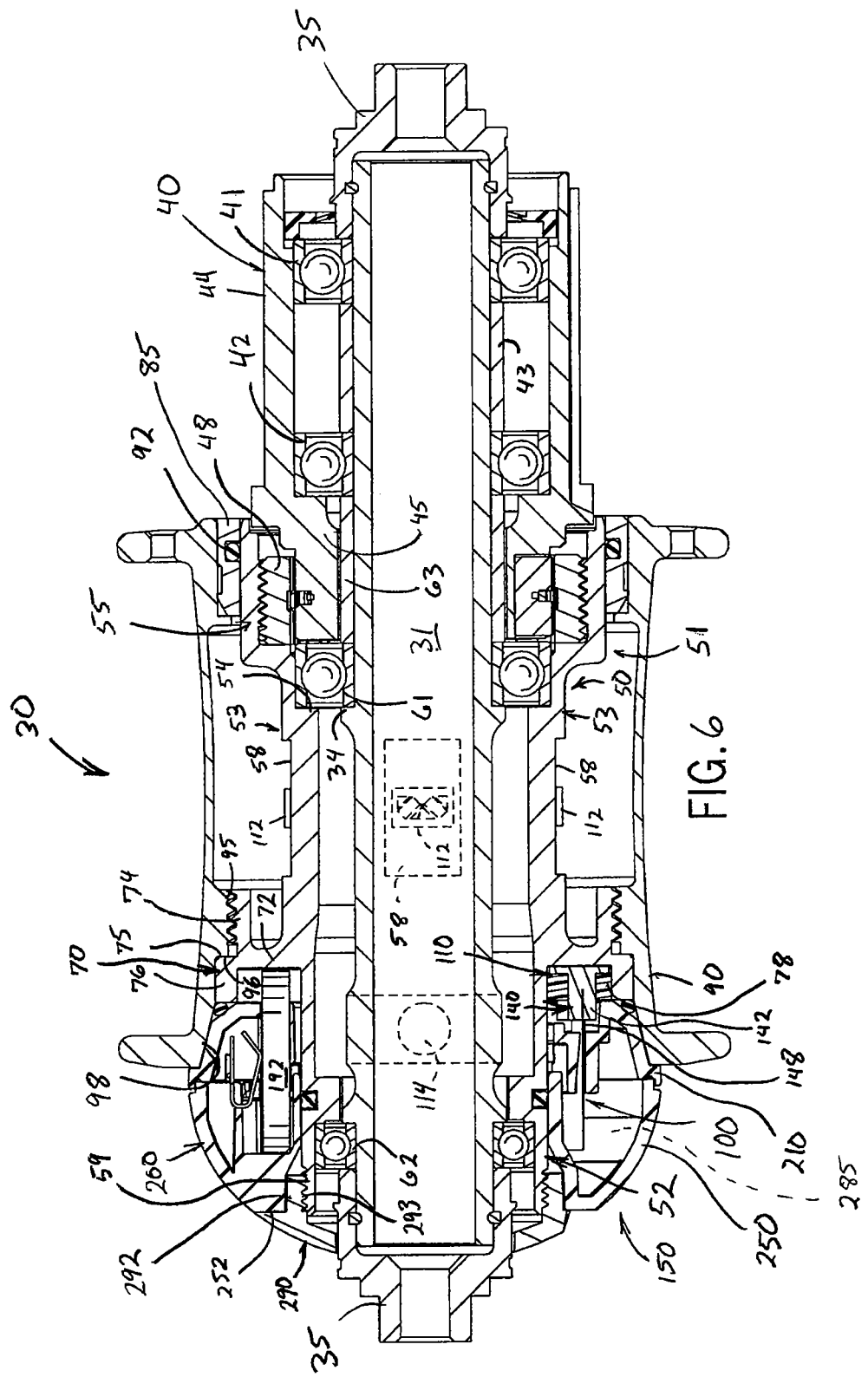
FIG. 6 is a cross-sectional view of the power-measuring hub assembly of FIG. 3, taken at line 6-6 of FIG. 3.

Referring now to FIGS. 5 and 6, a pair of spaced apart bearings 41, 42 rotationally mounts the free hub 40 to the axle 31. A spacer 43 is concentrically mounted over the axle 31 and is provided between the bearings 41, 42 to maintain their spaced apart relationship with each other. The free hub 40 includes lugs 44 that engage and upon which the driven sprocket(s) 9 (FIG. 1) are mounted so that rotation of the driven sprocket (s) 9 rotationally drives the free hub 40. A neck 45 of the free hub 40 engages a collar insert 48 (FIG. 6) that is threaded into a collar 55 at a first end 51 of the torque tube 50. The neck 45 of the free hub 40 and the collar insert 48 engage each other so that the torque tube 50 and hub shell 90 can overrun the free hub 40 in any of a variety of suitable known manners, such as, for example, a ratchet, sprag, and/or pawl-type engagement. Shown best in FIG. 1, by allowing the torque tube 50 (FIGS. 5 and 6) and hub shell 90 to overrun the driven sprocket(s) 9 in this way, the torque tube 50 and the hub shell 90 can also overrun the chain 10, crank chain ring 8, crank arms 6 and pedals 4.

Referring now to FIG. 6, the torque tube 50 is mounted for rotation with respect to and concentrically spaced from the axle 31 by way of a bearing 61 at the first end 51 of the torque tube 50 and a bearing 62 at a second end 52 of the torque tube 50. A spacer 63 is concentrically mounted over the axle 31 and is provided between the bearing 42 that supports the free hub 40 and the bearing 61 that supports the torque tube 50, such that the bearing 61 is longitudinally retained on the axle 31 between the spacer 63 and a shoulder 34 of the axle 31. The torque tube 50 is maintained by the bearing 61 in a longitudinal direction by a shoulder 54 of a main body 53 of the torque tube 50, adjacent the collar 55.

Still referring to FIG. 6, the main body 53 of the torque tube 50 extends between the collar 55 at the first end 51 and a flange 70 at the second end 52 of the torque tube 50. The flange 70 includes a web 72 that extends in a radial direction away from the main body 53 of the torque tube 50. The flange 70 further includes a threaded collar 74 that extends transversely away from the web 72, toward the first end 51 of the torque tube 50, so that the threaded collar 74 is radially spaced from the main body 53 of the torque tube 50. An outer collar 76 extends transversely away from the web 72, toward the second end 52 of the torque tube 50. The outer collar 76 is also radially spaced from the main body 53 and is positioned further from the main body 53 than the threaded collar 74, so that a shoulder 75 is defined between the threaded and outer collars 74, 76 of the flange 70.

Still referring to FIG. 6, at the first end 51 of the torque tube 50, a ring 85 is positioned concentrically between the collar 55 of the torque tube 50 and the hub shell 90 and an o-ring 92 is compressed between the collar 55 and ring 85. At the second end 52 of the torque tube 50, a threaded inner segment 95 of the hub shell 90 is received onto the threaded collar 74 of the torque tube flange 70. A shoulder 96 of the hub threaded inner segment 95 engages the shoulder 75 of the flange 70. An outer surface 77 of the outer collar 76 engages an inner surface 98 of the hub shell 90. In this way, the torque tube flange 70 and hub shell 90 cooperate as an alignment feature of the torque tube 50 within the power-measuring hub assembly 30, due to the outer collar 76 nesting against the inner surface 98 and shoulder 96 of the hub shell 90 and the threaded engagement of the threaded inner segment 95 of the hub shell 90 and threaded collar 74 of the flange 70. Such threaded engagement pulls the flange 70 into the hub shell 90 with a substantially constant squeezing pressure, continuously about an entire perimeter of an interface defined between the abutting shoulders 75, 96 of the flange 70 and hub shell 90. This prevents any localized relatively greater pinch force values that may be present if discrete fasteners were used to connect the flange 70 and hub shell 90 to each other. The engagement of the flange 70 and hub shell 90, in this way, maintains both (i) a concentricity of the torque tube 50 in the hub shell 90, and (ii) an angular alignment of the torque tube 50 and hub shell 90.

Referring now to FIGS. 4 and 5, the electronics system 100 of the power-measuring hub assembly 30 includes onboard electronics 110 and an electronics module 150. The onboard electronics 110 can be substantially permanently fixed to the power-measuring hub assembly 30, whereas the electronics module 150 is removably attached to the power-measuring hub assembly 30. A first, substantially fixed, connection interface is defined between the onboard electronics 110 and the power-measuring hub assembly 30 and a second, substantially removable connection interface is defined between the electronics module 150 and the power-measuring hub assembly 30. In the embodiment shown in FIGS. 4 and 6, the onboard electronics 110 is fixed to the torque tube 50. As shown in FIGS. 5 and 6, the onboard electronics 110 includes a printed circuit board 115 that has a receptacle 142. The printed circuit board 115 is sealed or adhered against the web 72 of the flange 70 and covered with a potting material 78 that can be any of a variety of suitable potting compounds, including various polymeric and epoxy materials. The potting material 78 encapsulates the printed circuit board 115 in a substantially liquid-tight coating, with the receptacle 142 extending out from the potting material 78. Although the onboard electronics 110 are shown as being fixed to the torque tube 50, it is understood that various components of the onboard electronics 110 may be instead fixed to the hub shell 90, so long as respective components of the electronics system 100 can remain suitably intact or connected during a disassembly of the power sensing system 20 to store a calibration value of the torque tube 50 and eliminate a need to recalibrate the torque tube 50 during reassembly of the power sensing system 20.

Still referring to FIGS. 4 and 5, onboard electronics 110 includes sensors, shown in this example as strain gauges 112, which are attached to lands 58 on the main body 53 of the torque tube. Operation of strain gauges 112 by changing their resistances upon deformation is well known in the art and therefore not detailed here. Strain gauges 112 are operably connected to the printed circuit board 115 that includes a memory module 117 that stores the calibration value for the torque tube 50, a strain gauge amplifier 119, and may include various conductors and/or other circuitry. The strain gauges 112, memory module 117 and strain gauge amplifier 119 cooperate so that signals from the strain gauges 112 relating to their deformation and/or other stresses are initially processed so that signals or data leaving the onboard electronics 110 are conditioned or calibrated for receipt by the electronics module 150 that uses such signals or data from the onboard electronics 110 for determining the force or torque experience by the torque tube 50. It is understood that such determinations may be instead performed by the computer 16 (FIG. 1).

Still referring to FIGS. 4 and 5, the onboard electronics 110 also includes a reed switch (not shown) or other sensor 113 (FIG. 5) that is mounted to the torque tube 50 and is aligned with a stationary magnet 114 that is mounted to the non-rotating axle 31. The sensor 113 is operably connected to the printed circuit board 115 so that as the sensor 113 rotates past the stationary magnet 114, the sensor 113 sends signals to the printed circuit board 115 or elsewhere in the electronics system 100 that relate to the angular velocity of the rotating power-measuring hub assembly 30 and thus the driven rear wheel 12 (FIG. 1). Such signals from the sensor 113 are transmitted to the electronics module 150 and/or computer 16 (FIG. 1) for the determination of speed, wheel rpm, and/or other relevant values and can be used with torque related values based on the strain gauges 112 signals or data to determine power values.

Referring again to FIGS. 5 and 6, a connector assembly 140 couples the onboard electronics 110 and electronics module 150 to each other. The connector assembly 140 includes the receptacle 142 that is mounted to the printed circuit board 115 of the onboard electronics 110 and a conductor tab 148 that extends from the electronics module 150. When the connector assembly 140 is coupled so that the electronics module 150 is in a connected position (FIG. 6), the conductor tab 148 is received into the receptacle 142 so that signals and/or data can be transferred between the onboard electronics 110 and the electronics module 150.

Figure 7:
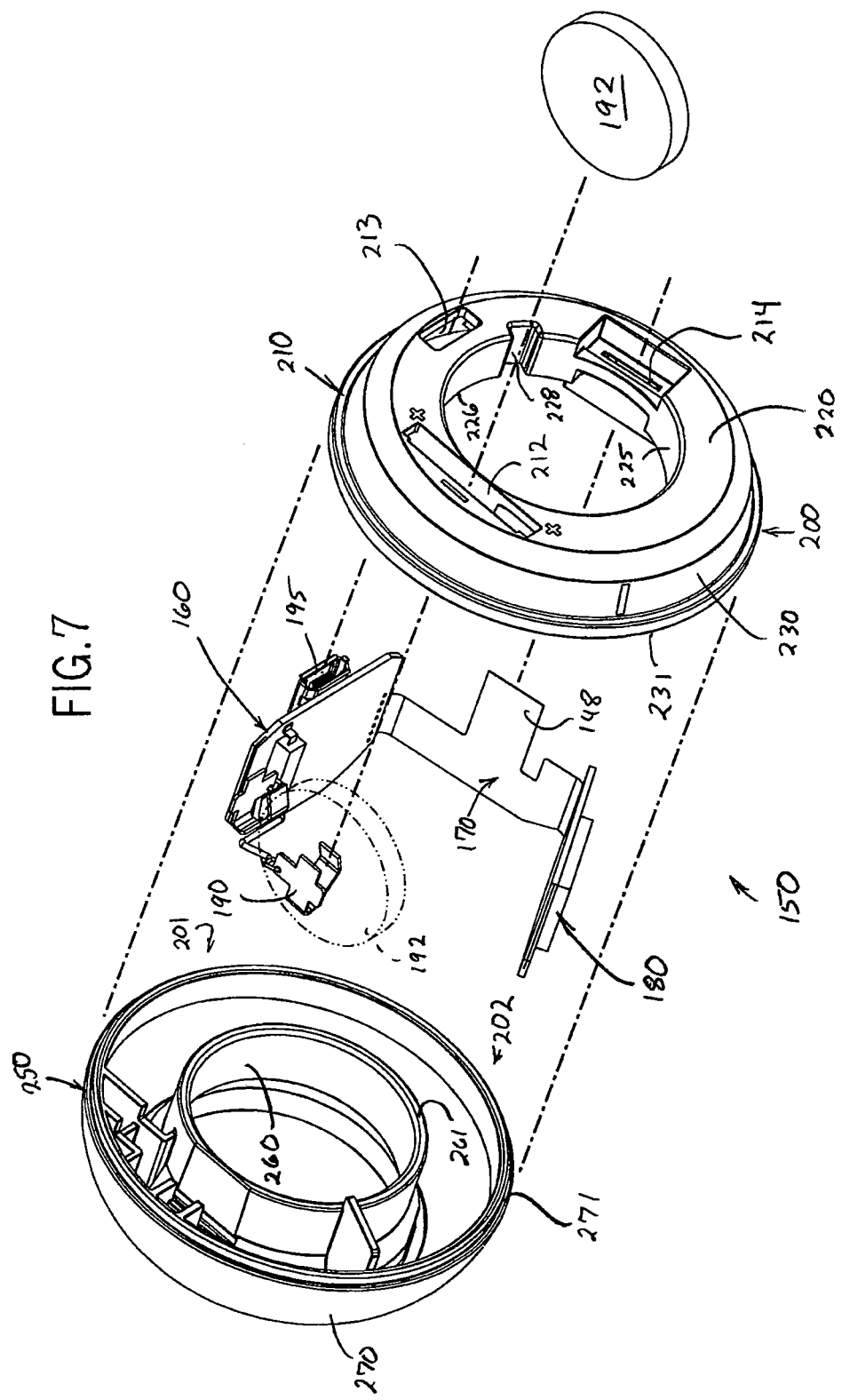
FIG. 7 is an exploded isometric view of an electronics module of the bicycle power sensing system of FIG. 1.

Referring now to FIG. 7, the electronics module 150 includes a first printed circuit board 160 and a second printed circuit board 180 that are mounted in opposing sides 201, 202 of an enclosure 200. A ribbon conductor 170 connects the first and second printed circuit boards 160, 180 to each other. The conductor tab 148 extends from the ribbon conductor 170 and is operably connected to each of the first and second printed circuit boards 160, 180 through the ribbon conductor 170. The first and second printed circuit boards 160, 180, at least together, include suitable circuitry and electronic components, such as microprocessors, analog-to-digital converters, amplifiers, RF or other receivers, RF or other transmitters, switches, bridges, memory modules, and/or other components that cooperate with each other for determining strain, torque, angular velocity and/or power in the power-measuring hub assembly 30 or transmitting signals or data to the computer 16 for such determinations.

Referring now to FIGS. 4 and 7, the various components of the electronics module 150 are housed within the enclosure 200 although some may be accessible from outside of the enclosure when the electronics module 150 is in a disconnected position (FIG. 4) and uncoupled from the rest of the power-measuring hub assembly 30. Enclosure 200 includes a base 210 and a cover 250. As shown in FIG. 7, a battery holder 190 is provided within the enclosure 200 and is connected to the first printed circuit board 160 (FIG. 7) so a battery 192 (FIG. 4) can provide power for the entire power-measuring hub assembly 30. The battery holder 190 is aligned with a first opening 212 that extends through an annular end wall 220 of the base 210. The battery 192 can be interested into and withdrawn from the battery holder 190 through the first opening 212. This allows the battery 192 to be replaced without separating the base 210 and cover 250 from each other.

Still referring to FIGS. 4 and 7, a data port 195 is provided within the enclosure 200 and is connected to the first printed circuit board 160 (FIG. 7). The data port 195 is aligned with a second opening 213 that extends through the end wall 220 of the base 210. Data port 195 is configured to accept a data cable (not shown) that connects the electronics module 150 to a computer (not shown), allowing data to be transferred therebetween. The data transferred through the data port 195 can relate to at least one of firmware for, failure diagnosis of, and performance data of, the bicycle power sensing system 20. Accordingly, the power-measuring hub assembly 30 can be software or firmware updated, performance analyzed, and/or trouble diagnosed, through the data port 195. Data port 195 is shown as a micro-USB port, although it is understood that other port configurations that allow the electronics module 150 to be temporarily connected to a computer can be used. It is further understood that such software or firmware updating, performance analyzing, and/or trouble diagnosing procedures can be done wirelessly instead of through the data port 195.

Still referring to FIGS. 4 and 7, a third opening 214 extends through the end wall 220 of base 210. The conductor tab 148 extends through and outwardly beyond the third opening 214. This allows the conductor tab 148 to be exposed when the electronics module 150 is detached from the rest of the power-measuring hub assembly 30, while the ribbon conductor 170 remains inside of the enclosure 200.

Still referring to FIGS. 4 and 7, base 210 include an inner wall 225 and an outer wall 230 that extend generally orthogonally from the inner and outer perimeters of the end wall 220, respectively, toward the cover 250. A keyway 228 extends into the inner wall 225 and in a longitudinal direction with respect to the enclosure 200. The keyway 228 engages a key 229 (FIG. 4) that extends radially from the second end 52 of the torque tube 50. The keyway 228 and key 229 cooperate to align the electronics module 150 with the torque tube 50 so that the flexible conductor tab 148 aligns with, for receipt into, the receptacle 142. The outer wall 230 tapers downwardly from adjacent the cover 250, toward the flange 70 of the torque tube 50. The tapering sidewall engages the hub shell 90 so that the end wall 220 is positioned longitudinally within the hub shell 90, so that the enclosure 200 is partially nested in the hub shell 90.

Referring now to FIGS. 6 and 7, the cover 250 includes an annular end wall 252 that faces away from the base 210 of the enclosure 200. An inner wall 260 of the cover 250 extends from the inner perimeter of the end wall 252 toward the base 210 and has a generally cylindrical configuration. An outer wall 270 extends from the outer perimeter of the end wall 252 along a curved path toward the base 210, which provides the outer wall 270 with a dome-like configuration. As shown in FIG. 7, edges 226, 261 of the inner walls 225, 260 of the base 210 and cover 250 engage each other. Also as shown in FIG. 7, edges 231, 271 of the outer walls 230, 270 of the base 210 and cover 250 engage each other. Respectively engaged edges 226, 261 and 231, 271 can be welded or otherwise joined together so as to define substantially liquid-tight seals between the base 210 and cover 250 at their locations of joinder. In this way, the electronic components of the electronics module 150 are housed within an annular cavity 285 (FIG. 6) that is defined between the base 210 and cover 250 and substantially liquid-tight connections are defined between the respective inner and outer walls 225, 260 and 230, 270 of the base 210 and cover 250.

Referring again to FIGS. 5 and 6, when the electronics module 150 is removably mounted to the remainder of the power-measuring hub assembly 30, in its connected position (FIG. 6) a hub o-ring 92 provides a seal between the hub shell 90 and the enclosure 200 and a shaft o-ring 36 provides a seal between the shaft 31 and the enclosure 200. As shown in FIG. 6, the hub o-ring 92 is compressed at an intersection of the outer collar 76 of the torque tube flange 70, the inner surface 98 of the hub shell 90, and the outer side wall 230 of the enclosure base 210. As also shown in FIG. 6, the shaft o-ring 36 is positioned in a circumferential groove 37 of the shaft 31 and is compressed into the circumferential groove 37 by the inner wall 260 of the enclosure cover 250.

Still referring to FIGS. 5 and 6, a cap nut 290 longitudinally secures the electronics module 150 against the torque tube 50 and hub shell 90. Cap nut 290 includes a neck 292 that is concentrically housed inside of the inner wall 260 of the cover 250 and concentrically outward of the end cap 35. The neck 292 of cap nut 290 has a threaded inner circumferential surface 293 that engages threads 59 of the second end 52 of the torque tube 50. Such threaded engagement of the threaded inner circumferential surface 293 of the neck 292 and the threads 59 of torque tube 50 holds the electronics module 150 tightly enough to maintain the electronics module 150 with its keyway 228 engaging the key 229 (FIG. 4) of the torque tube 50 and the conductor tab 148 in the receptacle 142 of the connector assembly 140. This allows the electronics module 150 to rotate in unison with the torque tube 50 and hub shell 90.

Referring now to FIGS. 1 and 6, to remove the electronics module 150 from the remainder of the power-measuring hub assembly 30, the user removes the driven rear wheel 12 from the bicycle 2. The cap nut 290 is unthreaded from its engagement with the threads 59 of the torque tube 50 and is removed.

The electronics module 150 can then be slid longitudinally away from the torque tube 50, which pulls the conductor tab 148 of the receptacle 142 and the keyway 228 over and past the key 229 (FIG. 4), separating the electronics module 150 from the onboard electronics 110, as shown in FIG. 4. This allows the battery 192 to be replaced, data accessed or diagnosis performed through, the data port 195, replacement of the entire electronics module 150, or sending of the electronics module 150 to a service center as a unit apart from the rest of the power-measuring hub assembly 30.

All of this can be done while preserving the integrity of the onboard electronics 110 and therefore without having to recalibrate the torque tube 50.

Various alternatives and embodiments are contemplated as being within the scope of the following claims particularly pointing out and distinctly claiming the subject matter regarded as the invention.

We claim:

1. A bicycle power sensing system comprising:
    a hub for supporting a driven wheel of a bicycle from an axle;
    a torque tube that can accept a driving torque and is connected to the hub so that the torque tube transmits the driving torque for rotating the driven wheel, the torque tube including:
        a sensor that detects the driving torque; and
        a memory module supported by at least one of the hub and the torque tube and storing a calibration value for the torque;
    an electronics module removably connected to the memory module; and
    an enclosure that houses the electronics module and is arranged for separating from the hub and the torque tube to disconnect the electronics module from the memory module while the memory module remains supported by the at least one of the hub and the torque tube.

2. The bicycle power sensing system of claim 1, the electronics module defining (i) a connected position in which the electronics module is connected to the torque tube so that the sensor and memory module of the torque tube communicate with the electronics module, and (ii) a disconnected position in which the electronics module is separated from the torque tube so that the sensor and memory module do not communicate with the electronics module.

3. The bicycle power sensing system of claim 2, further comprising a connector assembly having (i) a first connector that is provided on the torque tube and is in communication with at least one of the sensor and the memory module, and (ii) a second connector that is provided on and is in communication with the electronics module, wherein the first and second connectors engage and disengage each other when the electronics module is in the connected and disconnected positions, respectively.

4. The bicycle power sensing system of claim 1, wherein the electronics module selectively connects to the torque tube.

5. The bicycle power sensing system of claim 4, further comprising a connector assembly that can be connected so as to connect the electronics module to at least one of the sensor and memory module and disconnected so as to disconnect the electronics module from the at least one of the sensor and memory module.

6. The bicycle power sensing system of claim 5, wherein the connector assembly includes a first connector that has a conductor and a second connector that has a receptacle that receives the conductor.

7. A bicycle power sensing system comprising:
    a hub that supports a driven wheel of a bicycle;
    a torque tube that accepts a driving torque and transmits the driving torque to the hub for rotating the driven wheel; and
    a sensor attached to the torque tube for detecting the driving torque;
    a memory module connected to at least one of the hub and torque tube through a first connection interface; and
    an electronics module that communicates with at least one of the sensor and memory module and is connected to at least one of the hub and torque tube through a second connection interface, the second connection interface differing from the first connection interface, wherein the electronics module and memory module are configured and arranged such that the electronics module can be removed from the at least one of the hub and torque tube while the memory module remains connected to the at least one of the hub and torque tube.

8. The bicycle power sensing system of claim 7, wherein the memory module is fixedly connected to the at least one of the hub and torque tube.

9. The bicycle power sensing system of claim 8, the torque tube further comprising a flange and wherein the memory module is connected to the flange of the torque tube.

10. The bicycle power sensing system of claim 9, wherein the memory module is connected to the torque tube flange by at least one of an adhesive material and a potting material.

11. The bicycle power sensing system of claim 7, the electronics module further comprising an enclosure that engages at least one of the hub and the torque tube.

12. The bicycle power sensing system of claim 7, wherein the electronics module includes at least a first printed circuit board and a second printed circuit board that are mounted inside of the enclosure.

13. The bicycle power sensing system of claim 7, wherein the electronics module further comprises an enclosure and a battery holder for powering the bicycle power sensing system, wherein the battery holder is accessible from outside of the enclosure.

14. The bicycle power sensing system of claim 13, wherein the electronics module includes a data port through which data can be transferred between the electronics module and a computer, the data relating to at least one of a firmware for and a failure diagnosis of the bicycle power sensing system.

15. The bicycle power sensing system of claim 7, the electronics module further comprising an enclosure that is provided concentrically outside a portion of the torque tube.

16. The bicycle power sensing system of claim 15, wherein the enclosure includes a tapering wall that engages an inner circumferential surface of the hub.

17. The bicycle power sensing system of claim 15, wherein the enclosure includes an end wall that faces a flange extending radially from the torque tube.

18. The bicycle power sensing system of claim 17, wherein the memory module is provided between the flange of the torque tube and the enclosure of the electronics module.

19. The bicycle power sensing system of claim 7, further comprising a first connector operably connected to the memory module and a second connector operably connected to the electronics module, the first and second connectors releasably engaging each other to selectively electronically connect the memory and electronics modules.

20. The bicycle power sensing system of claim 19, wherein one of the first and second connectors includes a receptacle and the other one of the first and second connectors includes a conductor that can be received in the receptacle.

* * * * *